(12) United States Patent
Heeney et al.

(10) Patent No.: US 6,806,374 B2
(45) Date of Patent: Oct. 19, 2004

(54) MONO-, OLIGO- AND POLY-3-(1,1-DIFLUOROALKYL)THIOPHENES AND THEIR USE AS CHARGE TRANSPORT MATERIALS

(75) Inventors: Martin Heeney, Southampton (GB); Louise Farrand, Dorset (GB); Mark Giles, Southampton (GB); Marcus Thompson, Hampshire (GB); Steven Tierney, Southampton (GB); Maxim Shkunov, Southampton (GB); David Sparrowe, Dorset (GB); Iain McCulloch, Hampshire (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/201,575

(22) Filed: Jul. 24, 2002

(65) Prior Publication Data
US 2003/0062509 A1 Apr. 3, 2003

(30) Foreign Application Priority Data
Jul. 25, 2001 (EP) .............................. 01117651

(51) Int. Cl.$^7$ ........................ C07D 409/14; H01B 1/06; C08G 75/00
(52) U.S. Cl. .................... 549/59; 549/29; 528/377; 252/500; 252/299
(58) Field of Search ............... 549/29, 59; 528/377; 252/500, 299

(56) References Cited

U.S. PATENT DOCUMENTS

| | | | |
|---|---|---|---|
| 5,198,153 A | | 3/1993 | Angelopoulos et al. |
| 5,247,062 A | * | 9/1993 | Sawada et al. ............. 528/377 |
| 5,892,244 A | | 4/1999 | Tanaka et al. |
| 5,998,804 A | | 12/1999 | Suh et al. |
| 6,048,827 A | * | 4/2000 | Fukuchi ........................ 508/582 |
| 6,359,150 B1 | * | 3/2002 | Fukudome et al. ........... 549/59 |
| 6,414,164 B1 | * | 7/2002 | Afzali-Ardakani et al. ... 549/59 |
| 6,716,995 B2 | * | 4/2004 | Zhu et al. ...................... 549/62 |

FOREIGN PATENT DOCUMENTS

| | | |
|---|---|---|
| DE | 195 04 224 | 8/1995 |
| EP | 0 261 712 | 3/1988 |
| EP | 0 414 906 | 3/1991 |
| EP | 0 528 662 | 2/1993 |
| EP | 0 889 350 | 1/1999 |
| WO | WO 93/22397 | 11/1993 |
| WO | WO 95/22586 | 8/1995 |
| WO | WO 96/21659 | 7/1996 |
| WO | WO 97/00600 | 1/1997 |
| WO | WO 00/79617 | 12/2000 |

OTHER PUBLICATIONS

Naito, Katsuyuki, CA137:270136, 2002.*
Li, Ling et al, CA136:386423, 2002.*
Ritter et al, CA119:50397, 1993.*
Buchner, W. et al, CA118:124330, 1993.*

* cited by examiner

Primary Examiner—Deborah C. Lambkin
(74) Attorney, Agent, or Firm—Millen, White, Zelano & Branigan, P.C.

(57) ABSTRACT

Mono-, oligo- and polymers comprising one or more identical or different recurring units of formula I $$-[(Y)_a-(D)_b-(Z)_c]- \qquad I$$

wherein
D is a 3-(1,1-difluoroalkyl)thiophene group of formula II,

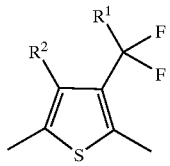

II wherein Y, Z, $R^1$, $R^2$, a, b and c have the meanings defined herein, are useful as semiconductors and charge transport materials.

51 Claims, No Drawings

MONO-, OLIGO- AND POLY-3-(1,1-DIFLUOROALKYL)THIOPHENES AND THEIR USE AS CHARGE TRANSPORT MATERIALS

FIELD OF INVENTION

The invention relates to new mono-, oligo- and poly-3-(1,1-difluoroalkyl)thiophenes, polymerisable liquid crystal materials and anisotropic polymer film, including their oxidatively or reductively doped forms. The invention further relates to methods of their preparation, their use as semiconductors or charge transport materials in optical, electrooptical or electronic devices including field effect transistors, electroluminescent, photovoltaic and sensor devices. The invention further relates to field effect transistors and semiconducting components comprising the new mono-, oligo- and poly-3-(1,1-difluoro-alkyl)thiophenes. Furthermore the invention relates to a security marking or device and to a charge injection layer, planarising layer, antistatic film or conducting substrate or pattern.

BACKGROUND AND PRIOR ART

Organic materials have recently shown promise as the active layer in organic based thin film transistors and organic field effect transistors (OFETs) [see reference 1]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1 \times 10^{-3}$ cm$^2$ V$^{-1}$ s$^{-1}$). In addition, it is important that the semiconducting material is relatively stable to oxidation i.e. it has a high ionisation potential, as oxidation leads to reduced device performance.

A known compound which has been shown to be an effective p-type semiconductor for OFETs is pentacene [see reference 2]. When deposited as a thin film by vacuum deposition, it was shown to have carrier mobilities in excess of 1 cm$^2$ V$^{-1}$ s$^{-1}$ with very high current on/off ratios greater than 10$^6$. However, vacuum deposition is an expensive processing technique that is unsuitable for the fabrication of large-area films.

Regioregular poly(3-hexylthiophene) has been reported with charge carrier mobility between $1 \times 10^{-5}$ and $4.5 \times 10^{-2}$ cm$^2$ V$^{-1}$ s$^{-1}$, but with a rather low current on/off ratio (10–10$^3$) [see reference 3]. In general, poly(3-alkylthiophenes) show good solubility and are able to be solution processed to fabricate large area films. However, poly(3-alkylthiophenes) have relatively low ionisation potentials and are susceptible to doping in air [see reference 4].

Fluorinated poly(alkylthiophenes) were studied by L. Robitaille and M. Leclerc [see reference 5]. However, poly (3'-perfluorohexylterthiophene was found to be insoluble and poly[3-(tridecafluorononyl)thiophene] to be soluble in octafluorotoluene, a solvent unsuitable for large scale solution processing. Compared to its alkyl analogues, however, it exhibits inferior electronic properties, which was attributed to lower regioregularity. In addition, the bulky fluoroalkyl group dilutes the macroscopic charge transport mobility arising from the conjugated pi-electron component of the molecule. This large group also potentially disrupts the closely packed lammelar morphology, again lowering mobility.

Perfluoro-α-sexithiophene and α,ω-diperfluorohexylsexithiophene are described as potential n-type semiconductors [see references 6, 7]. In fact, the α,ω-substituted sexithiophene exhibits carrier mobilities of up to $2 \times 10^{-2}$ cm$^2$ V$^{-1}$ s$^{-1}$ for electron transport (n-type semi-conduction). However, both fluorinated sexithiophenes have low solubilities in common solvents, and therefore may not be solution processed.

A perfluoralkylated heteroaromatic polymer represented by the general formula

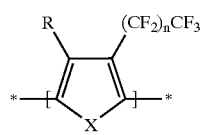

wherein R is H or alkyl, X is S, NH or O and n is 1 to 9, having a polymerization degree of 5 to 5000 is proposed in the EP 0 414 906 A1 [reference 8]. The polymer may be used as water- and oil-repellent and as an electrically conductive material. But again, the perfluoralkylated thiophenes show in general a low to very low solubility, especially in those organic solvents, which are commonly used in large scale production techniques.

It is the aim of the present invention to provide new materials for use as semiconductors or charge transport materials, which are easy to synthesize, have high charge mobility, good processibility especially a good solubility, and a good oxidative stability.

Further aims of the present inventions relate to advantageous uses of the mono-, oligo- and polymers, including their oxidatively or reductively doped forms, according to the invention.

Other aims of the invention are immediately evident to those skilled in the art from the following description.

The inventors have found that these aims can be achieved by providing new oligomers and polymers based on regioregular 3-(1,1-difluoro-alkyl)thiophenes, especially with a head-to-tail orientation. These oligo- and polymers exhibit a high degree of planarity in the backbone and strong interchain π—π stacking interactions making them effective charge transport materials with high charge carrier mobilities. The electron withdrawing 1,1-difluoro group adjacent to the thiophene ring lowers the HOMO (highest occupied molecular orbit) relative to the unfluorinated poly(3-alkyl) thiophenes. The oligo- and polymers according to the invention possess a sufficient high ionization potential and are sufficiently stable to oxidation. On the other side, these oligo- and polymers possess a good to very good solubility, especially in common organic solvents. Therefore the oligo- and polymers according to the invention are amenable to fast and economically favorable solution processing.

A further aspect of the invention relates to reactive mesogens consisting of a central core comprising one or more 3-(1,1-difluoro-alkyl)thiophene units, and optionally comprising further conjugated moieties that form an extended conjugated system together with the 3-(1,1-difluoro-alkyl)thiophene units, said core being linked, optionally via a spacer group, to one or two polymerisable groups. The reactive mesogens can induce or enhance liquid crystal phases or are liquid crystalline themselves. They can be ordered and aligned in their mesophase and the polymerisable group can be polymerised or crosslinked in situ to form coherent polymer films with a high degree of long range order, or monodomain, thus yielding improved semiconductor materials with high stability and high charge carrier mobility.

A further aspect of the invention relates to liquid crystal polymers, in particular liquid crystal side chain polymers obtained from the reactive mesogens according to the present invention, which are then further processed e.g. from solution as thin layers for use in semiconductor devices.

A further aspect of the invention relates to the mono-, oligo- and polymers, a material or polymer film according to the invention, which are oxidatively or reductively doped to form conducting ionic species. Another aspect of the invention is a charge injection layer, planarising layer, antistatic film or conducting substrate or pattern for electronic applications or flat panel displays, comprising mono-, oligo- or polymers, a material or polymer film according to this invention.

Definition of Terms

The terms 'liquid crystalline or mesogenic material' or 'liquid crystalline or mesogenic compound' means materials or compounds comprising one or more rod-shaped, lath-shaped or disk-shaped mesogenic groups, i.e. groups with the ability to induce liquid crystal phase behaviour. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'polymerisable' includes compounds or groups that are capable of participating in a polymerisation reaction, like radicalic or ionic chain polymerisation, polyaddition or polycondensation, and reactive compounds or reactive groups that are capable of being grafted for example by condensation or addition to a polymer backbone in a polymeranaloguous reaction.

The term 'film' includes self-supporting, i.e. free-standing, films that show more or less pronounced mechanical stability and flexibility, as well as coatings or layers on a supporting substrate or between two substrates.

SUMMARY OF THE INVENTION

The invention relates to mono-, oligo- and polymers comprising at least one 3-(1,1-difluoro-alkyl)thiophene group.

The invention further relates to the use of mono-, oligo- and polymers according to the invention as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of e.g. liquid crystal displays, for photovoltaic or sensor devices, as electrode materials in batteries, as photoconductors and for electrophotographic applications like electrophotographic recording.

The invention further relates to a field effect transistor, for example as a component of integrated circuitry, as a thin film transistor in flat panel display applications, or in a Radio Frequency Identification (RFID) tag, comprising one or more mono-, oligo- or polymers according to the invention.

The invention further relates to a semiconducting component, for example in OLED applications like electroluminescent displays or backlights of e.g. liquid crystal displays, in photovoltaic or sensor devices, as electrode materials in batteries, as photoconductors and for electrophotographic applications, comprising one or more mono-, oligo- or polymers according to the invention.

The invention further relates to a security marking or device comprising an RFID or ID tag or a FET according to the invention.

DETAILED DESCRIPTION OF THE INVENTION

The mono-, oligo- and poly-[3-(1,1-difluoroalkyl) thiophenes] according to the invention preferably comprise one or more identical or different recurring units of formula I $$-[(Y)_a-(D)_b-(Z)_c]-\qquad I$$

wherein

D is a 3-(1,1-difluoroalkyl)thiophene group of formula II

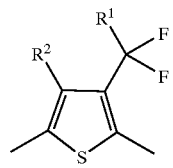

$R^1$ is H, straight chain, branched or cyclic alkyl with 1 to 20 C-atoms, which may be unsubstituted, mono- or partially-substituted by F, Cl, Br, I, —CN or —OH, it being also possible for one or more non-adjacent $CH_2$ groups to be replaced, in each case independently from one another, by —O—, —S—, —NH—, —NR°—, —SiR°R°°—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, $R^2$ is H, F, straight chain, branched or cyclic alkyl with 1 to 20 C-atoms, which may be unsubstituted, mono- or poly-substituted by F, Cl, Br, I, —CN or —OH, it being also possible for one or more non-adjacent $CH_2$ groups to be replaced, in each case independently from one another, by —O—, —S—, —NH—, —NR°—, —SiR°R°°—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, $R^0$ and $R^{00}$ are independently of each other H or alkyl with 1 to 12 C-atoms, Y and Z are independently of each other —$CX^1$=$CX^2$—, —C≡C—, or optionally substituted arylene or heteroarylene, $X^1$ and $X^2$ are independently of each other H, F, Cl or CN, and a, b and c are independently of each other 0 or 1, with a+b+c>0, and wherein in at least one recurring unit b is 1.

In the definition of $R^1$ "partially substituted" means that not all H-atoms are substituted by the given substituants, especially $R^1$ is not perfluorinated or perchlorinated.

The mono-, oligo- and poly-3-(1,1-difluoro-alkyl) thiophenes according to the invention are especially useful as charge transport semiconductors in that they have high carrier mobilities.

Particularly preferred are those mono-, oligo- and polymers wherein $R^1$ is an alkyl-group with 1 to 20 C-atoms, especially with 2 to 15 C-atoms, which may contain one $CF_2$- or $CF_3$-group, without being perfluorinated.

Additionally those mono-, oligo- and polymers according to the invention are preferred wherein $R^2$ is H, F or an optionally substituted alkyl-group with 1 to 20 C-atoms.

Particularly preferred are mono-, oligo- and polymers comprising at least one 3-(1,1-difluoro-alkyl)thiophene group and at least one reactive group that is capable of a polymerisation or crosslinking reaction.

Further preferred are mono-, oligo- and polymers comprising at least one 3-(1,1-difluoro-alkyl)thiophene group that are mesogenic or liquid crystalline.

Further preferred are oligo- and polymers comprising at least two recurring units, at least one of which is a recurring unit according to the invention.

Especially preferred are mono-, oligo- and polymers of formula I1

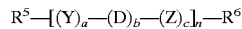   I1 wherein

Y, Z, D, a, b and c are as defined in formula I, n is an integer from 1 to 5000, $R^5$ and $R^6$ are independently of each other H, halogen, $Sn(R^0)_3$ or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —NR°—, —SiR°R°°—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or denote P—Sp—X, P is a polymerisable or reactive group, Sp is a spacer group or a single bond, and X is —O—, —S—, —OCH$_2$—, —CH$_2$O—, —CO—, —COO—, —OCO—, —OCO—O—, —CO—NR°—, —NR°—CO—, —OCH$_2$—, —CH$_2$O—, —SCH$_2$—, —CH$_2$S—, —CH=CH—COO—, —OOC—CH=CH— or a single bond, wherein $R^0$ and $R^{00}$ are as defined above and wherein the recurring units $[(Y)_a$—$(D)_b$—$(Z)_c]$ can be identical or different.

In the oligo- and polymers of the present invention the recurring units $(Y)_a$—$(D)_b$—$(Z)_c$ in case of multiple occurrence can be selected of formula I independently of each other, so that an oligo- or polymer may comprise identical or different recurring units $(Y)_a$—$(D)_b$—$(Z)_c$. The oligo- and polymers thus include homopolymers and copolymers like for example statistically random copolymers, for example with a monomer sequence such as —Y—D—Z—Z—D—Y—D—, alternating copolymers, for example with a monomer sequence such as —Y—D—Z—Y—D—Z—, and block copolymers, for example with a monomer sequence such as —Y—Y—D—D—D—Z—Z—Z—Z—, wherein the groups Y and Z form a conjugated system together with the 3-(1,1-difluoro-alkyl)thiophene unit D.

Especially preferred is the homopolymer.

Further preferred are mono-, oligo- and polymers comprising one or more recurring units $(Y)_a$—$(D)_b$—$(Z)c$, wherein a=c=0 and b=1, very preferably consisting exclusively of such recurring units.

Further preferred are mono-, oligo- and polymers comprising one or more recurring units $(Y)_a$—$(D)_b$—$(Z)_c$, wherein b=c=1 and a=0, very preferably consisting exclusively of such recurring units.

Further preferred are mono-, oligo- and polymers comprising one or more recurring units $(Y)_a$—$(D)_b$—$(Z)_c$, wherein a=b=c=1, very preferably consisting exclusively of such recurring units.

Further preferred are mono-, oligo- and polymers wherein n is an integer greater than 1, n is an integer from 2 to 5000, in particular from 30 to 1000, n is an integer from 2 to 5, n is an integer from 1 to 15 and one or both of $R^5$ and $R^6$ denote P—Sp—X, n is an integer from 2 to 5000 and $R^5$ and $R^6$ have one of the meanings of $R^2$, the molecular weight is from 30000 to 300000, $R^1$ is selected from $C_1$–$C_{20}$-alkyl that is optionally substituted with one or more fluorine atoms, but not perfluorinated, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, and optionally substituted aryl or heteroaryl, $R^1$ is a $C_1$–$C_{20}$-alkyl group, $R^2$ is selected from H, F, $C_1$–$C_{20}$-alkyl that is optionally substituted with one or more fluorine atoms, very preferably not perfluorinated, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, and optionally substituted aryl or heteroaryl, $R^2$ is selected from H, F or alkyl with 1 to 20 C-atoms, which is optionally substituted with one or more fluorine atoms, very preferably not perfluorinated, $R^5$ and $R^6$ are selected from H, halogen, $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl, in particular from H, halogen, $C_1$–$C_{20}$-alkyl and $C_1$–$C_{20}$-alkoxy, Y and Z are optionally substituted arylene or heteroarylene, Y and Z are —$CX^1$=$CX^2$— or —C≡C—, in at least one monomer unit $(Y)_a$—$(D)_b$—$(Z)_c$ a, b and c are 1, and one of Y and Z is arylene or heteroarylene and the other is —$CX^1$=$CX^2$— or —C≡C—, —$CX^1$=$CX^2$— is —CH=CH—, —CH=CF—, —CF=CH—, —CF=CF—, —CH=C(CN)— or —C(CN)=CH—, if n=b=1 and a=c=0, at least one of $R^5$ and $R^6$ is different from H.

A further preferred embodiment of the present invention relates to mono-, oligo- and polymers that are mesogenic or liquid crystalline, in particular those comprising one or more polymerisable groups. Very preferred materials of this type are monomers and oligomers of formula I1 wherein n is an integer from 1 to 15 and $R^5$ and/or $R^6$ denote P—Sp—X.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerisation or crosslinking via the groups P to yield polymer films with high charge carrier mobility and high thermal, mechanical and chemical stability.

It is also possible to copolymerise the polymerisable mono-, oligo- and polymers according to the invention with other polymerisable mesogenic or liquid crystal monomers that are known from prior art, in order to induce or enhance liquid crystal phase behaviour.

Thus, another aspect of the invention relates to a polymerisable liquid crystal material comprising one or more mono-, oligo- or polymers according to the invention comprising at least one polymerisable group, and optionally comprising one or more further polymerisable compounds, wherein at least one of the polymerisable mono-, oligo- and poly-3-(1,1-difluoroalkyl)thiophenes and/or the further polymerisable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the present invention relates to an anisotropic polymer film with charge transport properties obtainable from a polymerisable liquid crystal material as defined above that is aligned in its liquid crystal phase into macroscopically uniform orientation and polymerised or crosslinked to fix the oriented state.

Another aspect of the invention relates to a liquid crystal side chain polymer (SCLCP) obtained from a polymerisable liquid crystal material as defined above by polymerisation or polymeranaloguous reaction. Particularly preferred are SCLCPs obtained from one or more monomers according to formula I1 wherein one or both of $R^5$ and $R^6$ are a polymerisable or reactive group, or from a polymerisable mixture comprising one or more of such monomers of formula I1.

Another aspect of the invention relates to an SCLCP obtained from one or more monomers of formula I1 wherein one or both of $R^5$ and $R^6$ are a polymerisable group, or from a polymerisable liquid crystal mixture as defined above, by copolymerisation or polymeranaloguous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically<4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

Especially preferred are mono-, oligo- and polymers of the following formulae

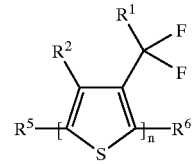

Ia

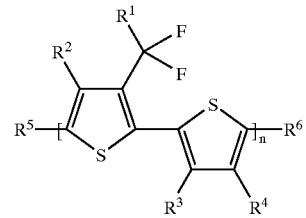

Ib

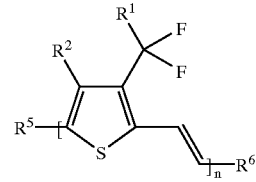

Ic

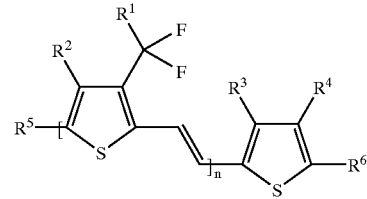

Id

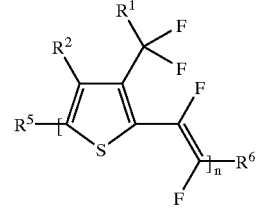

Ie

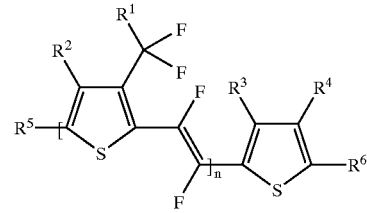

If

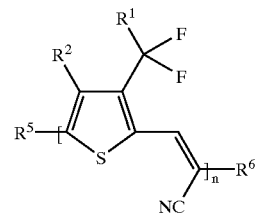

Ig

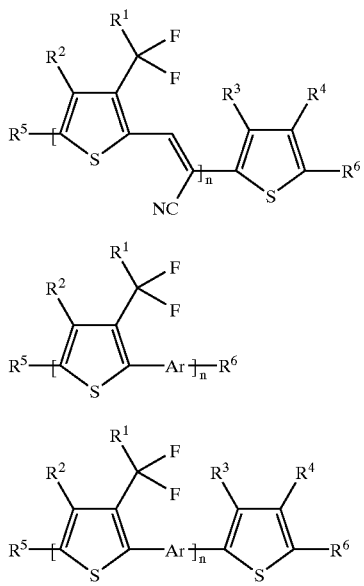

wherein
R¹ and R² have the meanings given in formula II,
R⁵, R⁶ and n have the meanings given in formula I1,
R³, R⁴ independently of each other have one of the meanings of R² given in formula II or are —CF₂—R¹,
Ar is a bivalent mono-, bi- or tricyclic aromatic or heteroaromatic group with up to 25 C atoms that may also comprise condensed rings and is optionally mono- or poly-substituted with F, Cl and/ or groups R² as defined in formula II.

In these preferred formulae, R² to R⁵ are very preferably H, F or alkyl with 1–16 C atoms that is optionally fluorinated, and Ar is very preferably 1,4-phenylene, alkoxyphenylene, alkylfluorene, thiophene-2,5-diyl, thienothiophene-2,5-diyl or dithienothiophene-2,6-diyl, all which may be substituted as defined for Ar. R¹ is preferably alkyl with 1–20 C-atoms, especially with 2–15 C-atoms. R³, R⁴ have preferably the meanings of R² and/or —CF₂—R¹. Very preferably R³ has the same meaning as R² and R⁴ is —CF₂—R¹.

Aryl and heteroaryl preferably denote a mono-, bi- or tricyclic aromatic or heteroaromatic with up to 25 C atoms, wherein the rings may be fused, and in which the heteroaromatic groups contain at least one hetero ring atom, preferably selected from N, O and S. The aryl and heteroaryl groups are optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O, —S—CO—, —CO—S—, —CH=CH— or —C≡C— in such a manner that O and/or S atoms are not linked directly to one another.

Especially preferred aryl and heteroaryl groups are phenyl in which, in addition, one or more CH groups may be replaced by N, naphthalene, thiophene, thienothiophene, dithienothiophene, fluorene and oxazole, all of which can be unsubstituted, mono- or polysubstituted with L, wherein L is halogen or an alkyl, alkoxy, alkylcarbonyl or alkoxycarbonyl group with 1 to 12 C atoms, wherein one or more H atoms may be replaced by F or Cl.

Arylene and heteroarylene preferably denote a mono-, bi- or tricyclic divalent aromatic or heteroaromatic radicals with up to 25 C atoms, wherein the rings may be fused, and in which the heteroaromatic groups contain at least one hetero ring atom, preferably selected from N, O and S. The arylene and heteroarylene groups are optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH₂ groups are optionally replaced, in each case independently from one another, by —O—, —S—, —NH—, —NR⁰—, —SiR⁰R⁰⁰—, —CO—, —COO—, OCO—, —OCO—O, —S—CO—, —CO—S—, —CH=CH— or —C≡C— in such a manner that O and/or S atoms are not linked directly to one another.

If in the formulae shown above and below one of R¹ to R⁶ is an alkyl or alkoxy radical, i.e. where the terminal CH₂ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Especially preferred meanings of R¹ are linear alkyl chains of the formula —C$_q$H$_{2q+1}$, wherein q is an integer from 2 to 15.

Oxaalkyl, i.e. where one CH₂ group is replaced by —O—, is preferably straight-chain 2-oxapropyl(=methoxymethyl), 2-(=ethoxymethyl) or 3-oxabutyl(=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

Fluoroalkyl is preferably C$_i$F$_{2i+1}$, wherein i is an integer from 1 to 15, in particular CF₃, C₂F₅, C₃F₇, C₄F₉, C₅F₁₁, C₆F₁₃, C₇F₁₅ or C₈F₁₇, very preferably C₆F₁₃.

Halogen is preferably F or Cl.

The polymerisable or reactive group P is preferably selected from CH₂=CW¹—COO—,

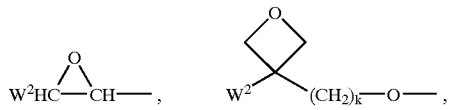

CH₂=CW²—(O)$_{k1}$—, CH₃—CH=CH—O—, HO—CW²W³—, HS—CW²W³—, HW²N—, HO—CW²W³—NH—, CH₂=CW¹—CO—NH—,

CH$_2$=CH—(COO)$_{k1}$—Phe—(O)$_{k2}$—, Phe—CH=CH—, HOOC—, OCN— and W$^4$W$^5$W$^6$Si—, with W$^1$ being H, Cl, CN, phenyl or alkyl with 1 to 5 C-atoms, in particular H, Cl or CH$_3$, W$^2$ and W$^3$ being independently of each other H or alkyl with 1 to 5 C-atoms, in particular methyl, ethyl or n-propyl, W$^4$, W$^5$ and W$^6$ being independently of each other Cl, oxaalkyl or oxacarbonylalkyl with 1 to 5 C-atoms, Phe being 1,4-phenylene and k, and k$_2$ being independently of each other 0 or 1.

Especially preferred groups P are CH$_2$=CH—COO—, CH$_2$=C(CH$_3$)—COO—, CH$_2$=CH—, CH$_2$=CH—O— and

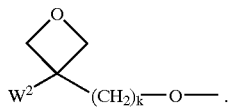

Very preferred are acrylate and oxetane groups. Oxetanes produce less shrinkage upon polymerisation (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to those skilled in the art. The spacer group Sp is preferably a linear or branched alkylene group having 1 to 20 C atoms, in particular 1 to 12 C atoms, in which, in addition, one or more non-adjacent CH$_2$ groups may be replaced by —O—, —S—, —NH—, —N(CH$_3$)—, —CO—, —O—CO—, —S—CO—, —O—COO—, —CO—S—, —CO—O—, —CH(halogen)-, —C(halogen)$_2$—, —CH(CN)—, —CH=CH— or —C≡C—, or a siloxane group.

Typical spacer groups are for example —(CH$_2$)$_p$—, —(CH$_2$CH$_2$O)$_r$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, r being an integer from 1 to 3 and R$^0$ and R$^{00}$ having the meanings given in formula I.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene for example.

Further preferred are compounds with one or two groups P—Sp—X wherein Sp and/or X is a single bond.

In case of compounds with two groups P—Sp—X, each of the two polymerisable groups P, the two spacer groups Sp, and the two linkage groups X can be identical or different.

SCLCPs obtained from the inventive compounds or mixtures by polymerisation or copolymerisation have a backbone that is formed by the polymerisable group P in formula I1.

The mono-, oligo- and polymers of the present invention can be synthesized according to or in analogy to known methods. Some preferred methods are described below.

Regioregular Head-to-tail Poly[3-(1,1-difluoroalkyl) thiophenes] (4)

Starting from commercially available 3-cyanothiophene (5), a route to poly[3-(1,1-difluoroalkyl)thiophenes] (4) is outlined below.

Scheme 1:

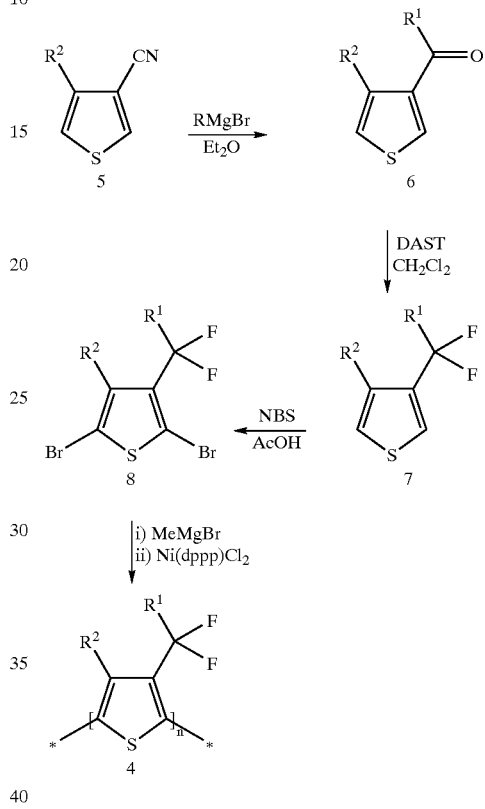

3-Cyanothiophene (5) is alkylated using the alkyl Grignard to yield ketothiophene (6), via hydrolysis of the intermediate imine. Ketothiophene (6) is converted into a thiolane (70 by treatment with a dithiol in the presence of boron trifluoride. Fluorination of thiolane (7) using NBS in pyridinium poly (hydrogen fluoride) afforded 1,1-difluoroalkylthiophene (7) as a mixture containing the mono- and dibromothiophenes (see reference 9). The crude mixture was further brominated with NBS in DMF to afford dibromodifluoroalkylthiophene (8) after distillation. Poly[3-(1,1-difluoroalkyl)thiophene] (4) is synthesised from (8) by the route described by Rieke [see reference 10]. Treatment with one equivalent of active zinc forms the arylzinc reagent. Addition of a catalytic amount of Ni(dmpe)Cl$_2$, where dppp is 1,2-bis (dimethylphosphino)ethane, affords regioregular head-to-tail poly[3-(1,1-difluoroalkyl)thiophene] (4).

Two alternative strategies for forming the key 1,1-difluoroalkylthiophene (7) intermediate are outlined in scheme 2.

Scheme 2:

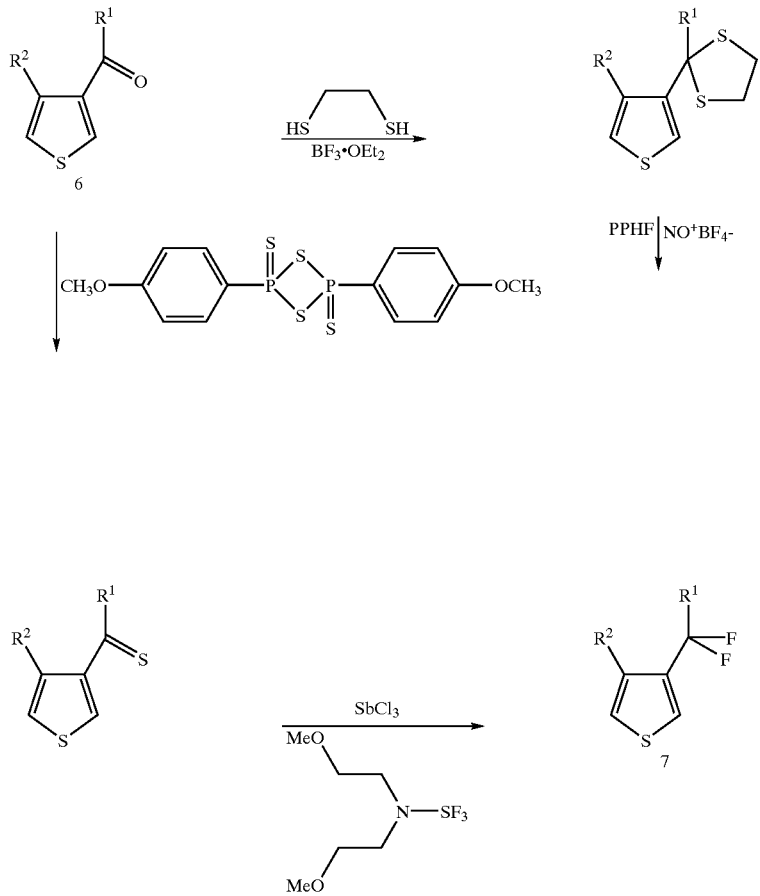

The ketothiophene (6) intermediate is converted into a thioketone by reaction with Lawessons reagent (2,4-bis(4-methoxyphenyl)-1,3,2,4-dithiadiphosphetan-2,4-dithione). The thioketone is converted into (7) by treatment with bis(2-methoxyethyl)aminosulfur trifluoride [see reference 11]. Alternatively intermediate (6) is converted directly into 1,1-difluoroalkylthiophene (7) using (diethylamino)sulfur trifluoride (DAST) or equivalent [see reference 12].

Other coupling routes to polymer (7) are Stille coupling [see reference 13], McCullough coupling [see reference 14, 15], and Suzuki coupling [see reference 16].

Reactive mesogens comprising an 3-(1,1-difluoro-alkyl) thiophene mono- or oligomeric group and one or two polymerisable groups P—Sp—X can be prepared for example according to or in analogy to the following synthesis routes.

According to scheme 3,3-(1,1-difluoro-alkyl)thiophene (7) is brominated in the 2-position by one equivalent of N-bromo-succinimide in acetic acid to yield (9). Cross-coupling of the dihalo 3-(1,1-difluoro-alkyl)thiophene (9) with an alkyl Grignard reagent in the presence of a nickel catalyst yields mono-alkyl alcohol (10). Lithiation of (10) in the 5-position, followed by oxidative coupling affords (11). Routine methodology converts the protected bis-alcohol (11) into the bis-acrylate or bis-oxetane.

Scheme 3:

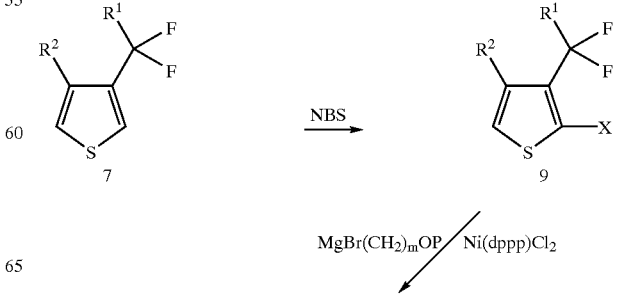

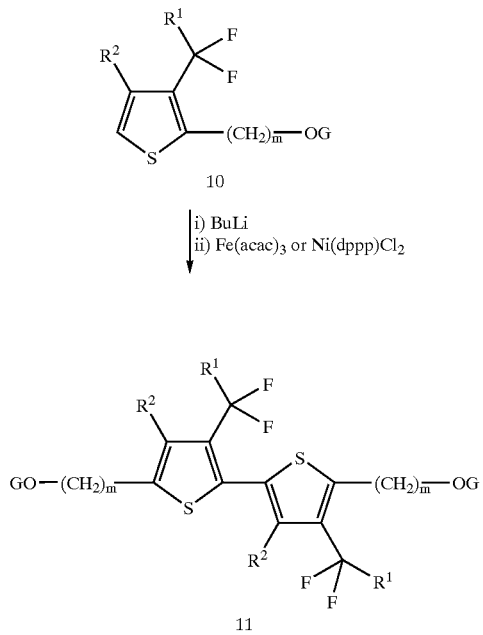

wherein m is an integer e.g. from 1 to 20 and G is a protecting group.

3-(1,1-difluoro-alkyl)thiophene Polymers Containing Conjugated Groups $CX^1=CX^2$ or Ar The Stille coupling of 2,5-dibromo-3-(1,1-difluoro-alkyl) thiophene (8) with the bis-organotin reagent (12) yields polymer (13) containing $CX^1=CX^2$ groups [see reference 17].

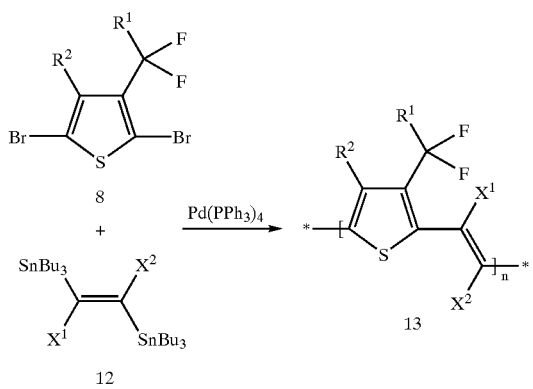

The Suzuki coupling of 2,5-dibromo-3-(1,1-difluoro-alkyl)thiophene (8) with bis-boronic acid (14) yields polymer (15) containing aryl groups.

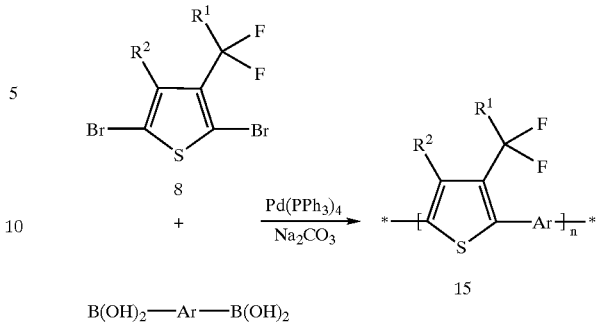

A further aspect of the invention relates to both the oxidised and reduced form of the compounds and materials according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g. $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns ot tracts in electronic applications such as printed circuit boards and condensers.

Mono-, oligo- and polymers according to the present invention that comprise one or more groups P—Sp—X can be polymerised, or copolymerised with other polymerisable compounds, via the polymerisable group P. This is preferably done by in-situ polymerisation of a coated layer of the material, preferably during fabrication of the electronic or optical device comprising the inventive semiconductor material. In case of liquid crystal materials, these are preferably aligned in their liquid crystal state into homeotropic orientation prior to polymerisation, where the conjugated pi-electron systems are orthogonal to the direction of charge transport. This ensures that the intermolecular distances are minimised and hence then energy required to transport charge between molecules is minimised. The molecules are then polymerised or crosslinked to fix the uniform orientation of the liquid crystal state. Alignment and curing are carried out in the liquid crystal phase or mesophase of the material. This technique is known in the art and is generally described for example in D. J. Broer, et al., Angew. Makromol. Chem. 183, (1990), 45–66

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Mono-, oligo- and polymers comprising one or more groups P—Sp—X can also be copolymerised with polymerisable mesogenic compounds to induce, or, in case of mesogenic materials of formula I, enhance liquid crystal phase behaviour. Polymerisable mesogenic compounds that are suitable as comonomers are known in prior art and disclosed for example in WO 93/22397; EP 0,261,712; DE 195,04,224; WO 95/22586 and WO 97/00600.

SCLCPs can be prepared from the polymerisable compounds or mixtures according to the invention by the methods described above, or by conventional polymerisation techniques which are known to those skilled in the art, including for example radicalic, anionic or cationic chain polymerisation, polyaddition or polycondensation. Polymerisation can be carried out for example as polymerisation in solution, without the need of coating and prior alignment, or polymerisation in situ. It is also possible to form SCLCPs by grafting compounds according to the invention with a suitable reactive group, or mixtures thereof, to presynthesized isotropic or anisotropic polymer backbones in a polymeranaloguous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added e.g. to polysiloxane backbones with Si—H groups. It is also possible to form SCLCPs by copolymerisation or polymeranaloguous reaction from the inventive compounds together with conventional mesogenic or non mesogenic comonomers. Suitable comonomers are known to those skilled in the art. In principle it is possible to use all conventional comonomers known in the art that carry a reactive or polymerisable group capable of undergoing the desired polymer-forming reaction, like for example a polymerisable or reactive group P as defined above. Typical mesogenic comonomers are for example those mentioned in WO 93/22397; EP 0,261,712; DE 195,04,224; WO 95/22586 and WO 97/00600. Typical non mesogenic comonomers are for example alkyl mono- or diacrylates or alkyl mono- or dimethacrylates with alkyl groups of 1 to 20 C atoms, like methyl acrylate or methyl methacrylate, trimethylpropane trimethacrylate or pentaerythritol tetraacrylate.

Especially the oligomers and polymers according to the invention show advantageous solubility properties which allow production processes using solutions of these compounds. Thus films, including layers and coatings, may be generated by low cost production techniques e.g. spin coating. Suitable solvents or solvent mixtures comprise alkanes and/or aromatics, especially their fluorinated derivatives. Preferred solvents are propylene glycol monoethyl acetate, methoxy propanol, ethyl lactate, cyclohexanone and cyclopropanone and mixtures comprising one or more of these solvents.

The mono-, oligo- and poly-3-(1,1-difluoro-alkyl) thiophenes of the present invention are useful as optical, electronic and semiconductor materials, in particular as charge transport materials in field effect transistors (FETs), as photovoltaics or sensor materials, for electrophotographic applications, and for other semiconductor applications. Such FETs, where an organic semiconductive material is arranged as a film between a gate-dielectric and a drain and a source electrode, are generally known, e.g. U.S. Pat. No. 5,892,244, WO 00/79617, U.S. Pat. No. 5,998,804, also see references 1, 18 and 19. The solubility properties of these materials according to the invention, allow amenability to solution processing, and therefore low cost, high volume manufacture by techniques such as reel to reel coating is possible. Preferred applications of these FETs are therefore such as integrated circuitry, TFT-displays and security applications. In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Alternatively, the mono-, oligo- and polymers according to the invention may be used in organic light emitting devices or diodes (OLEDs), e. g. in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see e. g. Meerholz, Synthetic Materials, 111–112, 2000, 31–34, Alcala, J. Appl. Phys., 88, 2000, 7124–7128 and the literature cited therein.

According to another use, the inventive compounds, materials or films, especially those which show photoluminescent properties, may be employed as materials of light sources, e.g. of display devices such as described in EP 0 889 350 A1 or by C. Weder et al., Science, 279, 1998, 835–837.

References
1. H. E. Katz, Z. Bao and S. L. Gilat, *Acc. Chem. Res.*, 2001, 34, 5, 359.
2. S. F. Nelson, Y. Y. Lin, D. J. Gundlach and T. N. *Jackson, Appl. Phys. Lett.*, 1998, 72, 1854.
3. Z. Bao, A. Dodabalapur and A. J. Lovinger, *Appl. Phys. Lett.*, 1996, 69, 4108.
4. H. Sirringhaus, N. Tessler, D. S. Thomas, P. J. Brown, R. H. Friend, *Adv. Solid State Phys.*, 1999, 39, 101.
5. L. Robitaille and M. Leclerc, *Macromol.* 1994, 27, 1847–1851.
6. Y. Sakamoto, et al., *J. Am. Chem. Soc.*, 2001, 123, 4643–4644.
7. A. Facchetti, et al., *Angew. Chem. Int. Ed.*, 2000, 39, 4547–4551.
8. EP 0 414 906 A1.
9. C. York, et al., *Tetrahedron*, 1996, 52, 9–14.
10. T.-A. Chen, R. D. Rieke, *J. Am. Chem. Soc.*, 1992, 114, 10087.
11. G. S. Lal, A. Evans, *J. Org. Chem.*, 2000, 65, 4830–4832.
12. W. J. Middelton, *J. Org. Chem.*, 1975, 40, 574.
13. D. Milstein, J. K. Stille, *J. Am. Chem. Soc.*, 1979, 101, 4992.
14. Loewe, R. S., S. M. Khersonsky, and R. D. McCullough, *Advanced Materials*, 1999. 11(3), 250–253.
15. Loewe, R. S., et al., *Macromolecules*, 2001, 34, 4324–4337.
16. N. Miyaura, T. Yanagi, A. Suzuki, *Synth. Commun.*, 1981, 11, 513.
17. R. S. Loewe and R. D. McCullough, *Chem. Mater.*, 2000, 12, 3214.
18. H. Fuchigami, A. Tsumura, H. Koezuka, *Appl. Phys. Lett.*, 1993, 63, 1372–1374.
19. H. Sirringhaus, N. Tessler, R. H. Friend, *Science*, 1998, 280, 1741–1744.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding corresponding European application No. 01117651.8 is hereby incorporated by reference.

EXAMPLES

Example 1

3-(1'-hexanoyl)thiophene (6)

3-Cyanothiophene (20.0 g, 0.183 mol) was dissolved in anhydrous diethyl ether (100 ml) and cooled to 0° C. A solution of pentylmagnesium bromide (2M in diethylether, 100 ml) was added dropwise via a dropping funnel. The reaction was allowed to warm to RT and stirred for 16 h. The reaction was quenched with 5% HCl (150 ml) and stirred for 1 h. The organic layer was separated and the aqueous layer extracted with THF (3×100 ml). The combined organics were washed with brine, dried ($Na_2SO_4$), filtered and concentrated under reduced pressure to afford a dark oil (33.14 g, 99%). Purity (HPLC)=97%. MS (El) M=182 ($M^+$). The $^1H$ NMR was consistent with the proposed structure.

Example 2

Thiolane Protected Thiophene 7

3-(1'-hexanoyl)thiophene (33.14 g, 0.182 mol) and ethanedithiol(32 ml, 0.382 mol) were stirred under nitrogen and boron trifluoride acetic acid complex ( (27.8 ml, 0.2 mol) was added dropwise. The reaction was stirred for 16 h at RT. Further dithiol (5 ml) and $BF_3$.HOAc (5 ml) were added and the reaction stirred for a further 24 h. The reaction was diluted with petrol (200 ml) and quenched with sat. $NaHCO_3$ (100 ml). The layers were separated and the organic layer was washed with 5% NaOH (3×50 ml), brine, dried ($Na_2SO_4$), filtered and concentrated under reduced pressure to afford a crude oil (44 g). This was further purified by column chromatography (eluent petrol, then petrol:DCM 7:3) to afford 7 (30.9 g, 66%). Purity (HPLC)=99%. MS (El) M=258 ($M^+$). The $^1H$ NMR was consistent with the proposed structure.

Example 3

2,5-dibromo-3-(1',1'-difluorohexyl)thiophene (8)

Recrystallised NBS (45.45 g, 255 mmol) was dissolved in anhydrous DCM (350 ml) in a PFA flask and cooled to −78C. 70% Pyridinium poly(hydrogen fluoride) (PPHF, 30 ml) was added via a plastic syringe, followed by the dropwise addition of thiolane (7). The reaction was stirred for 1 h at −78C., and then diluted with petrol (100 ml) and filtered through a plastic cloumn containing neutral alumina (100 g).

The resulting solution was stirred over anhydrous KF to remove HF residues and concetrated under reduced pressure to afford a crude oil (15.02 g). The was dissolved in DMF (200 ml) and NBS (45 g, 255 mmol) was added portionwise. The resulting mixture was stirred for 16 h in the the absence of light. The DMF was distilled under reduced pressure and the crude residue filtered thorugh silica (eluent: petrol) to afford a crude brown oil (10.5 g). This was further purified by bulb-to-bulb distillation (100 C., 0.4 mbar) to afford 8 (5.71 g, 27%). Purity HPLC+.MS (El) M=362 (t, M$^+$). The $^1$H, $^{13}$C and $^{19}$F NMR were consistent with the proposed structure.

Example 4

Poly[3-(1,1-difluoroalkyl)thiophene (4)

In a dry weighed schlenk tube was added a solution of Rieke zinc in THF (aldrich) and the THF removed under reduced pressured to afford 0.21 g (3.2 mmol) of active zinc. This was redissolved in dry THF (15 ml) and cooled to −78 C. 2,5-Dibromo-3-(1',1'-difluorohexyl)thiophene (0.88 g, 2.43 mmol) was added via a syringe and the reaction allowed to warm to RT over 20 min. Stirred for 2 h at RT until complete mono zic insertion was observed by GC (quenched sample). Stirring was halted and the ecess zinc allowed to settle. In a separate schlenk flask Ni(dmpe)Cl$_2$ (9.7 mg, 1 mol %) was stirred in THF (5 ml). The organozinc reagent was transferred via cannula into the solution of catalyst at 0° C. The solution was warmed to 60° C. for 96 h, cooled and poured into methanol (50 ml) containing 10% HCl (10 ml). The resulting suspension was filtered and washed with methanol (3×10 ml), petrol (3×10 ml), and acetone (3×10 ml) to remove inorganics and low MW material. The resulting solid was dissolved in THF and reprecipitated into methanol, filtered and dried to afford poly[3-(1,1-difluoroalkyl)thiophene as a red solid (101 mg, 18%). Gel permeation chromatography shows Mw 7300 Daltons, Mn 5800 Daltons. $\lambda_{max}$ (THF) 438 nm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A monmeric, oligomeric, or polymeric [3-(1,1-difluoroalkyl)thiophene] compound comprising one or more identical or different recurring units of formula I

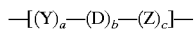   I wherein

D is a 3-(1,1-difluoroalkyl)thiophene group of formula II

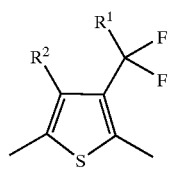   II

R$^1$ is H, straight chain, branched or cyclic alkyl with 1 to 20 C-atoms, which is unsubstituted, mono- or partially-substituted by F, Cl, Br, I, —CN or —OH, wherein optionally one or more non-adjacent CH$_2$ groups is replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH═CH— or —C≡C— in such a manner that O and/or S atoms are not linked directly to one another, or optionally substituted aryl or optionally substituted heteroaryl, R$^2$ is H, F, straight chain, branched or cyclic alkyl with 1 to 20 C-atoms, which is unsubstituted, mono- or poly-substituted by F, Cl, Br, I, —CN or —OH, wherein optionally one or more non-adjacent CH$_2$ groups is replaced, in each case independently from one another, by —O—, —S—, —NH—, —NR$^o$—, —SiR$^o$R$^{oo}$—, —CO—, —COO—, —OCO—, —OCO—O—, —CO—, —CO—S—, —CH═CH— or —C≡C— in such a manner that O and/or S atoms are not linked directly to one another, or optionally substituted aryl or optionally substituted heteroaryl, R$^o$ and R$^{oo}$ are independently of each other H or alkyl with 1 to 12 C-atoms, Y and Z are independently of each other —CX$^1$═CX$^2$—, —C≡C—, or optionally substituted arylene or heteroarylene, X$^1$ and X$^2$ are independently of each other H, F, Cl or CN, and a, b and c are independently of each other 0 or 1, with a+b+c>0, and wherein in at least one recurring unit b is 1, wherein if n and b both equal 1 and a and c both equal 0, then at least one of the terminal groups of the compound is not H.

2. A compound according to claim 1, wherein said compound has at least one reactive group that is capable of a polymerization or crosslinking reaction.

3. A compound according to claim 1, wherein said compound is mesogenic or liquid crystalline.

4. An oligomeric or polymeric compound according to claim 1, wherein said compound comprises at least two recurring units, at least one of which is a recurring unit of formula I.

5. A compound according to claim 1, wherein said compound is selected from formula I1

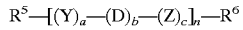   I1 wherein n is an integer from 1 to 5000,

R$^5$ and R$^6$ are independently of each other H, halogen, Sn(R$^o$)$_3$ or straight chain, branched or cyclic alkyl with 1 to 20 C-atoms, which is unsubstituted, mono- or poly-substituted by F, Cl, Br, I or CN, wherein optionally one or more non-adjacent CH$_2$ groups is replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH═CH— or —C≡C— in such a manner that O and/or S atoms are not linked directly to one another, or optionally substituted aryl or optionally substituted heteroaryl, or denote P—Sp—X, P is a polymerizable or reactive group, Sp is a spacer group or a single bond, and X is —O—, —S—, —OCH$_2$—, —CH$_2$O—, —CO—, —COO—, —OCO—, —OCO—O—, —CO—NR$^o$—, —NR$^o$—CO—, —OCH$_2$—, —CH$_2$O—, —SCH$_2$—, —CH$_2$S—, —CH═CH—COO—, —OOC—CH═CH— or a single bond, wherein the recurring units $[(Y)_a-(D)_b-(Z)_c]$ can be identical or different.

6. A compound according to claim 5, wherein said compound is selected from the following formulae

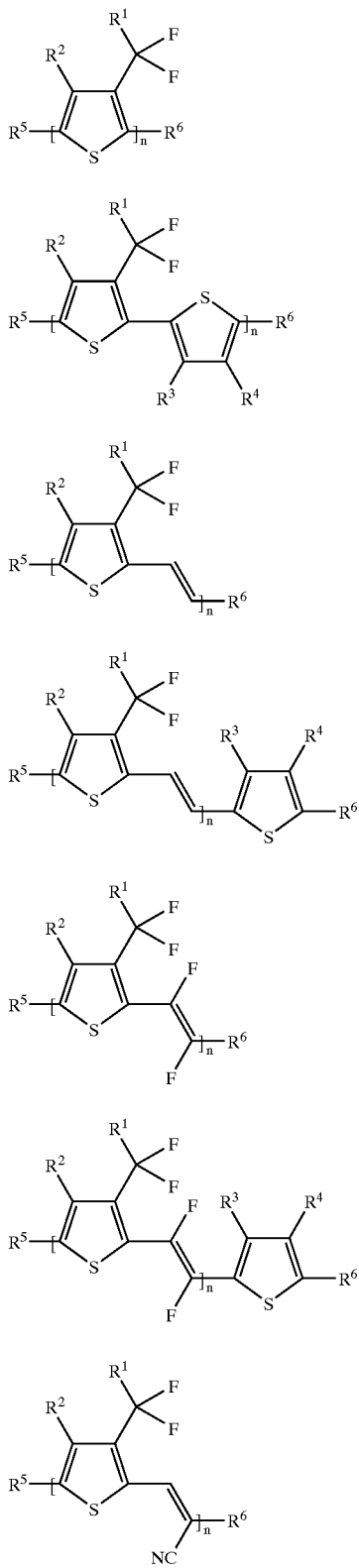

a b c d e f g

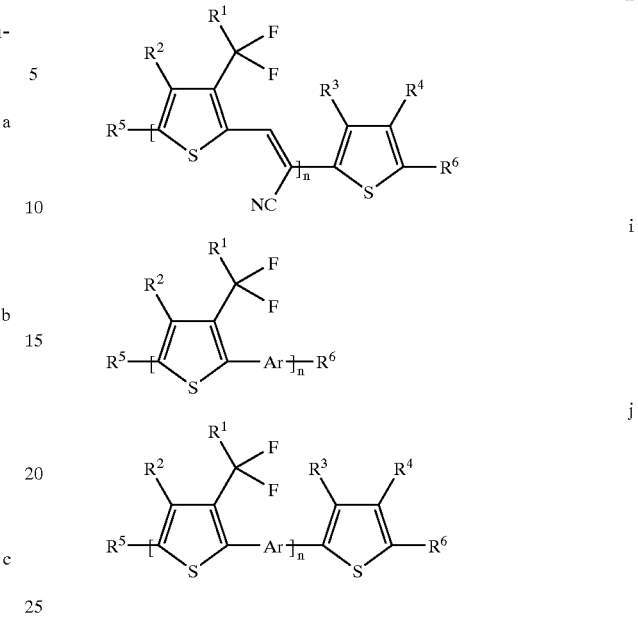

h i j wherein
$R^3$, $R^4$ are each, independently of each other, H, F, straight chain, branched or cyclic alkyl with 1 to 20 C-atoms, which is unsubstituted, mono- or poly-substituted by F, Cl, Br, I, —CN or —OH, wherein optionally one or more non-adjacent $CH_2$ groups is replaced, in each case independently from one another, by —O—, —S—, —NH—, —NR$^o$—, —SiR$^o$R$^{oo}$—, —CO—, —COO—, —OCO—, —OCO—O—, —CO—, —CO—S—, —CH=CH— or —C≡C— in such a manner that O and/or S atoms are not linked directly to one another, or optionally substituted aryl or optionally substituted heteroaryl, or is a group —CF$_2$—R$^1$, and Ar is a bivalent mono-, bi- or tricyclic aromatic or heteroaromatic group with up to 25 C atoms wherein the rings may be fused, and is optionally mono- or poly-substituted with F, Cl and/or straight chain, branched or cyclic alkyl with 1 to 20 C-atoms, which is unsubstituted, mono- or poly-substituted by F, Cl, Br, I, —CN or —OH, wherein optionally one or more non-adjacent $CH_2$ groups is replaced, in each case independently from one another, by —O—, —S—, —NH—, —NR$^o$—, —SiR$^o$R$^{oo}$—, —CO—, —COO—, —OCO—, —OCO—O—, —CO—, —CO—S—, —CH=CH— or —C≡C— in such a manner that O and/or S atoms are not linked directly to one another.

7. A compound according to claim 5, wherein $R^5$ and $R^6$ are independently of each other H, halogen, Sn(R$^o$)$_3$ or straight chain, branched or cyclic alkyl with 1 to 20 C-atoms, which is unsubstituted, mono- or poly-substituted by F, Cl, Br, I or CN, wherein optionally one or more non-adjacent $CH_2$ groups is replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in sch a manner that O and/or S atoms are not linked directly to one another, or optionally substituted aryl or optionally substituted heteroaryl.

8. A compound according to claim 6, wherein $R^5$ and $R^6$ are independently of each other H, halogen, Sn(R$^o$)$_3$ or straight chain, branched or cyclic alkyl with 1 to 20 C-atoms, which is unsubstituted, mono- or poly-substituted by F, Cl, Br, I or CN, wherein optionally one or more non-adjacent $CH_2$ groups is replaced, in each case independently from one another, by —O—, —S—, —NH—, $—NR^0—$, $—SiR^0R^{00}—$, —CO—, —COO—, —OCO—, —OCO—O—, —S—CO—, —CO—S—, —CH=CH— or —C≡C— in sch a manner that O and/or S atoms are not linked directly to one another, or optionally substituted aryl or optionally substituted heteroaryl.

9. A compound according to claim 5, wherein one or both of $R^5$ and $R^6$ is a group P—Sp—X.

10. A compound according to claim 6, wherein one or both of $R^5$ and $R^6$ is a group P—Sp—X.

11. A compound according to claim 5, wherein
P is selected from $CH_2=CW^1—COO—$,

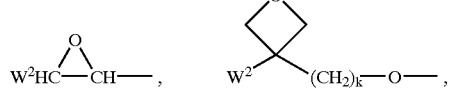

$CH_2=CW^2—(O)_{k1}—$, $CH_3—CH=CH—O—$,
$HO—CW^2W^3—$, $HS—CW^2W^3—$, $HW^2N—$,
$HO—CW^2W^3—NH—$, $CH_2=CW^1—CO—NH—$,
$CH_2=CH—(COO)_{k1}—Phe—(O)_{k2}—$, Phe—CH=CH—, HOOC—, OCN— and $W^4W^5W^6Si—$, $W^1$ is H, Cl, CN, phenyl or alkyl with 1 to 5 C-atoms,
$W^2$ and $W^3$ are each independently of each other H or alkyl with 1 to 5 C-atoms,
$W^4$, $W^5$ and $W^6$ are each independently of each other Cl, oxaalkyl or oxacarbonylalkyl with 1 to 5 C-atoms,
Phe is 1,4-phenylene, and
$k_1$ and $k_2$ are each independently of each other 0 or 1.

12. A compound according to claim 6, wherein
P is selected from $CH_2=CW^1—COO—$,

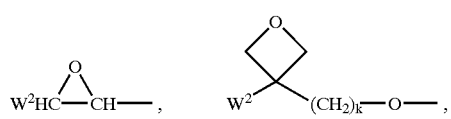

$CH_2=CW^2—(O)_{k1}—$, $CH_3—CH=CH—O—$,
$HO—CW^2W^3—$, $HS—CW^2W^3—$, $HW^2N—$,
$HO—CW^2W^3—NH—$, $CH_2=CW^1—CO—NH—$,
$CH_2=CH—(COO)_{k1}—Phe—(O)_{k2}—$, Phe—CH=CH—, HOOC—, OCN— and $W^4W^5W^6Si—$, $W^1$ is H, Cl, CN, phenyl or alkyl with 1 to 5 C-atoms,
$W^2$ and $W^3$ are each independently of each other H or alkyl with 1 to 5 C-atoms,
$W^4$, $W^5$ and $W^6$ are each independently of each other Cl, oxaalkyl or oxacarbonylalkyl with 1 to 5 C-atoms,
Phe is 1,4-phenylene, and
$k_1$ and $k_2$ are each independently of each other 0 or 1.

13. A compound according to claim 7, wherein
P is selected from $CH_2=CW^1—COO—$,

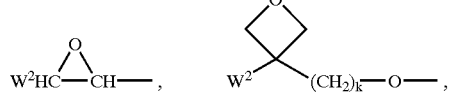

$CH_2=CW^2—(O)_{k1}—$, $CH_3—CH=CH—O—$,
$HO—CW^2W^3—$, $HS—CW^2W^3—$, $HW^2N—$,
$HO—CW^2W^3—NH—$, $CH_2=CW^1—CO—NH—$,
$CH_2=CH—(COO)_{k1}—Phe—(O)_{k2}—$, Phe—CH=CH—, HOOC—, OCN— and $W^4W^5W^6Si—$, $W^1$ is H, Cl, CN, phenyl or alkyl with 1 to 5 C-atoms,
$W^2$ and $W^3$ are each independently of each other H or alkyl with 1 to 5 C-atoms,
$W^4$, $W^5$ and $W^6$ are each independently of each other Cl, oxaalkyl or oxacarbonylalkyl with 1 to 5 C-atoms,
Phe is 1,4-phenylene, and
$k_1$ and $k_2$ are each independently of each other 0 or 1.

14. A compound according to claim 9, wherein
P is selected from $CH_2=CW^1—COO—$,

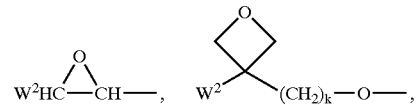

$CH_2=CW^2—(O)_{k1}—$, $CH_3—CH=CH—O—$,
$HO—CW^2W^3—$, $HS—CW^2W^3—$, $HW^2N—$,
$HO—CW^2W^3—NH—$, $CH_2=CW^1—CO—NH—$,
$CH_2=CH—(COO)_{k1}—Phe—(O)_{k2}—$, Phe—CH=CH—, HOOC—, OCN— and $W^4W^5W^6Si—$, $W^1$ is H, Cl, CN, phenyl or alkyl with 1 to 5 C-atoms,
$W^2$ and $W^3$ are each independently of each other H or alkyl with 1 to 5 C-atoms,
$W^4$, $W^5$ and $W^6$ are each independently of each other Cl, oxaalkyl or oxacarbonylalkyl with 1 to 5 C-atoms,
Phe is 1,4-phenylene, and
$k_1$ and $k_2$ are each independently of each other 0 or 1.

15. A compound according to claim 5, wherein n is an integer from 1 to 15.

16. A compound according to claim 6, wherein said compound is of formula Ia and n is 1.

17. A polymerizable liquid crystal material comprising one or more compounds according to claim 1 having at least one polymerizable group, and optionally one or more further polymerizable compounds, wherein at least one of said one or more compounds and/or at least one of said further polymerizable compounds is mesogenic or liquid crystalline.

18. An anisotropic polymer film with charge transport properties obtainable from a polymerizable liquid crystal material according to claim 17 that is aligned in its liquid crystal phase into macroscopically uniform orientation and polymerized or crosslinked to fix the oriented state.

19. A side chain liquid crystal polymer obtained by polymerization of one or more monomeric or oligomeric compounds according to claim 1, or by grafting one or more of said monomeric or oligomeric compounds to a polymer backbone in a polymeranaloguous reaction, optionally with one or more additional mesogenic or non-mesogenic comonomers.

20. A side chain liquid crystal polymer obtained by polymerization of a polymerizable material according to claim 17, or by grafting said polymerizable material to a polymer backbone in a polymeranaloguous reaction, optionally with one or more additional mesogenic or non-mesogenic comonomers.

21. In an optical, electrooptical or electronic device containing a semiconductor or charge transport material, the improvement wherein said semiconductor or charge transport material comprises a compound according to claim 1.

22. A field effect transistor (FET), OLED, electroluminescent device, RFID tag, backlight, photovoltaic or sensor device, or electrophotographic recording device comprising one or more compounds according to claim 1.

23. A field effect transistor (FET), OLED, electroluminescent device, RFID tag, backlight, photovoltaic or sensor device, or electrophotographic recording device comprising a polymerizable material of claim 17.

24. A field effect transistor (FET), OLED, electroluminescent device, RFID tag, backlight, photovoltaic or sensor device, or electrophotographic recording device comprising an anisotropic film of claim 18.

25. A field effect transistor (FET), OLED, electroluminescent device, RFID tag, backlight, photovoltaic or sensor device, or electrophotographic recording device comprising one or more polymers of claim 19.

26. A security marking or device comprising one or more compounds of claim 1.

27. A security marking or device comprising a polymerisable material of claim 17.

28. A security marking or device comprising an anisotropic film according to claim 18.

29. A security marking or device comprising one or more polymers of claim 19.

30. A security marking or device comprising a FET or RFID tag according to claim 22.

31. A compound according to claim 1, which is oxidatively or reductively doped to form conducting ionic species.

32. A polymerizable material according to claim 17, which is oxidatively or reductively doped to form conducting ionic species.

33. An anisotropic film according to claim 18, which is oxidatively or reductively doped to form conducting ionic species.

34. A polymer according to claim 19, which is oxidatively or reductively doped to form conducting ionic species.

35. A charge injection layer, planarising layer, antistatic film or conducting substrate or pattern for electronic applications or flat panel displays, comprising a compound according to claim 31.

36. A charge injection layer, planarising layer, antistatic film or conducting substrate or pattern for electronic applications or flat panel displays, comprising a polymerizable material according to claim 32.

37. A charge injection layer, planarising layer, antistatic film or conducting substrate or pattern for electronic applications or flat panel displays, comprising an anisotropic film according to claim 33.

38. A charge injection layer, planarising layer, antistatic film or conducting substrate or pattern for electronic applications or flat panel displays, comprising a polymer according to claim 34.

39. In an optical, electrooptical or electronic device containing a semiconductor or charge transport material, the improvement wherein said semiconductor or charge transport material comprises a polymerisable material according to claim 17.

40. In an optical, electrooptical or electronic device containing a semiconductor or charge transport material, the improvement wherein said semiconductor or charge transport material comprises a polymer according to claim 19.

41. A compound according to claim 1, wherein said compound is a homopolymer.

42. A compound according to claim 1, wherein a is 0, c is 0 and b is 1.

43. A compound according to claim 1, wherein b is 1, c is 1 and a is 0.

44. A compound according to claim 1, wherein b is 1, c is 1 and a is 1.

45. A compound according to claim 1, wherein n is an integer from 2 to 5.

46. A compound according to claim 1, wherein n is an integer from 1 to 15 and one or both of $R^5$ and $R^6$ is P—Sp—X.

47. A compound according to claim 1, wherein $R^1$ is selected from $C_1$–$C_{20}$-alkyl that is optionally substituted with one or more fluorine atoms, but not perfluorinated, $C_1$–$C_{20}$-alkenyl, $C_1$–$C_{20}$-alkynyl, $C_1$–$C_{20}$-alkoxy, $C_1$–$C_{20}$-thioether, $C_1$–$C_{20}$-silyl, $C_1$–$C_{20}$-ester, $C_1$–$C_{20}$-amino, and optionally substituted by aryl or heteroaryl.

48. A compound according to claim 1, wherein $R^1$ is a $C_1$–$C_{20}$-alkyl group.

49. A compound according to claim 1, wherein Y and Z are —$CX^1$=$CX^2$— or —C≡C—.

50. A compound according to claim 1, wherein in at least one monomer unit $(Y)_a$—$(D)_b$—$(Z)_c$ a, b and c are 1, and one of Y and Z is arylene or heteroarylene and the other is —$CX^1$=$CX^2$— or —C≡C—.

51. A compound according to claim 1, wherein —$CX^1$=$CX^2$— is —CH=CH—, —CH=CF—, —CF=CH—, —CF=CF—, —CH=C(CN)— or —C(CN)=CH—.

\* \* \* \* \*